(12) United States Patent
Oluigbo

(10) Patent No.: US 9,731,071 B2
(45) Date of Patent: Aug. 15, 2017

(54) SYSTEM AND METHOD FOR REGULATING ENDOGENOUS NEUROMODULATORY AGENT LEVELS

(71) Applicant: The Ohio State University, Columbus, OH (US)

(72) Inventor: Chima O. Oluigbo, Columbus, OH (US)

(*) Notice: Subject to any disclaimer, the term of this patent is extended or adjusted under 35 U.S.C. 154(b) by 1074 days.

(21) Appl. No.: 13/865,467

(22) Filed: Apr. 18, 2013

(65) Prior Publication Data

US 2013/0289521 A1 Oct. 31, 2013

Related U.S. Application Data

(60) Provisional application No. 61/639,319, filed on Apr. 27, 2012.

(51) Int. Cl.
| | |
|---|---|
| *A61M 31/00* | (2006.01) |
| *A61M 5/172* | (2006.01) |
| *A61K 9/00* | (2006.01) |
| *A61B 5/00* | (2006.01) |

(52) U.S. Cl.
CPC ......... *A61M 5/1723* (2013.01); *A61B 5/4094* (2013.01); *A61B 5/4839* (2013.01); *A61K 9/0085* (2013.01); *A61B 5/6868* (2013.01); *A61B 2562/028* (2013.01)

(58) Field of Classification Search
CPC . A61M 5/1723; A61B 5/4839; A61B 5/14546
USPC ........................................................ 604/503
See application file for complete search history.

(56) References Cited

U.S. PATENT DOCUMENTS

| | | | |
|---|---|---|---|
| 2003/0171711 A1* | 9/2003 | Rohr | A61B 5/14546 604/67 |
| 2005/0042753 A1* | 2/2005 | Yang | A61K 47/4823 435/455 |
| 2005/0153885 A1 | 7/2005 | Yun et al. | |
| 2008/0288018 A1 | 11/2008 | Rezai et al. | |

* cited by examiner

*Primary Examiner* — Edelmira Bosques
(74) *Attorney, Agent, or Firm* — Tarolli, Sundheim, Covell & Tummino LLP

(57) ABSTRACT

One aspect of the present disclosure includes a closed-loop therapy delivery system for regulating an endogenous level of a first neuromodulatory agent in a subject. The therapy delivery system includes a sensing component, a delivery component, and a controller. The sensing component is configured to detect an extracellular level of the first neuromodulatory agent. The delivery component is configured to deliver an amount of a second neuromodulatory agent to an intraparenchymal target site of the subject. The controller is configured to coordinate operation of the sensing component and the delivery component.

5 Claims, 4 Drawing Sheets

SYSTEM AND METHOD FOR REGULATING ENDOGENOUS NEUROMODULATORY AGENT LEVELS

RELATED APPLICATION

This application claims the benefit of the U.S. Provisional Patent Application Ser. No. 61/639,319, filed Apr. 27, 2012, the entirety of which is hereby incorporated by reference.

TECHNICAL FIELD

The present disclosure relates to a system and method for precisely regulating endogenous neuromodulatory agent levels, and in particular to a closed-loop system and method for managing epilepsy and other neurological disorders.

BACKGROUND

Epilepsy is a disorder of the brain characterized by chronic, recurring seizures. Seizures are a result of uncontrolled discharges of electrical activity in the brain. A seizure typically manifests as sudden, involuntary, disruptive, and often destructive sensory, motor, and cognitive phenomena. Seizures are frequently associated with physical harm to the body (e.g., tongue biting, limb breakage, and burns), a complete loss of consciousness, and incontinence. A typical seizure, for example, might begin as spontaneous shaking of an arm or leg and progress over seconds or minutes to rhythmic movement of the entire body, loss of consciousness, and voiding of urine or stool.

A single seizure most often does not cause significant morbidity or mortality, but severe or recurring seizures (epilepsy) results in major medical, social, and economic consequences. Epilepsy is most often diagnosed in children and young adults, making the long-term medical and societal burden severe for this population of patients. People with uncontrolled epilepsy are often significantly limited in their ability to work in many industries and cannot legally drive an automobile. An uncommon, but potentially lethal form of seizure is called status epilepticus, in which a seizure continues for more than 30 minutes. This continuous seizure activity may lead to permanent brain damage, and can be lethal if untreated.

While the exact cause of epilepsy is uncertain, epilepsy can result from head trauma (such as from a car accident or a fall), infection (such as meningitis), or from neoplastic, vascular or developmental abnormalities of the brain. Most epilepsy, especially forms that are resistant to treatment (i.e., refractory), are idiopathic or of unknown causes, and is generally presumed to be an inherited genetic disorder. Demographic studies have estimated the prevalence of epilepsy at approximately 1% of the population, or roughly 2.5 million individuals in the United States alone. Approximately 60% of these patients have epilepsy where a specific focus can be identified in the brain and, thus, such patients are candidates for some form of a focal treatment approach.

To assess possible causes and to guide treatment, epileptologists (both neurologists and neurosurgeons) typically evaluate people with seizures with brain wave electrical analysis (e.g., electroencephalography or and electrocorticogram) and imaging studies, such as magnetic resonance imaging. While there is no known cure for epilepsy, chronic usage of anticonvulsant and antiepileptic medications can control seizures in most people. The anticonvulsant and antiepileptic medications do not actually correct the underlying conditions that cause seizures. Instead, the anticonvulsant and antiepileptic medications manage the patient's epilepsy by reducing the frequency of seizures. There are a variety of classes of antiepileptic drugs (AEDs), each acting by a distinct mechanism or set of mechanisms.

For most cases of epilepsy, the disease is chronic and requires chronic medications for treatment. AEDs generally suppress neural activity by a variety of mechanisms, including altering the activity of cell membrane ion channels and the propensity of action potentials to be generated. Precise control over delivery of such medications is imperative as improper dosing can lead to undesired side effects, such as over-sedation, gingival hyperplasia (a cosmetically undesirable overgrowth of the gums), and/or a thickening of the skull (as occurs with phenyloin).

SUMMARY

One aspect of the present disclosure includes a closed-loop therapy delivery system for regulating an endogenous level of a first neuromodulatory agent in a subject. The therapy delivery system includes a sensing component, a delivery component, and a controller. The sensing component is configured to detect an extracellular level of the first neuromodulatory agent. The delivery component is configured to deliver an amount of a second neuromodulatory agent to an intraparenchymal target site of the subject. The controller is configured to coordinate operation of the sensing component and the delivery component Another aspect of the present disclosure includes a method for regulating an endogenous level of a first neuromodulatory agent in a subject. One step of the method includes implanting a closed-loop therapy delivery system in the subject. The therapy delivery system includes at least one sensing component configured to detect an extracellular level of the first neuromodulatory agent, a delivery component configured to deliver a second neuromodulatory agent to an intraparenchymal target site of the subject, and a controller configured to coordinate operation of the sensing component and the delivery component. Next, the endogenous level of the first neuromodulatory agent is sensed by the sensing component. The delivery component is then activated to adjust application of the second neuromodulatory agent in response to the sensed level of the first neuromodulatory agent. The sensing and delivery steps are automatically repeated until the endogenous level of the first neuromodulatory agent is within a normal physiological range.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Figure 1:
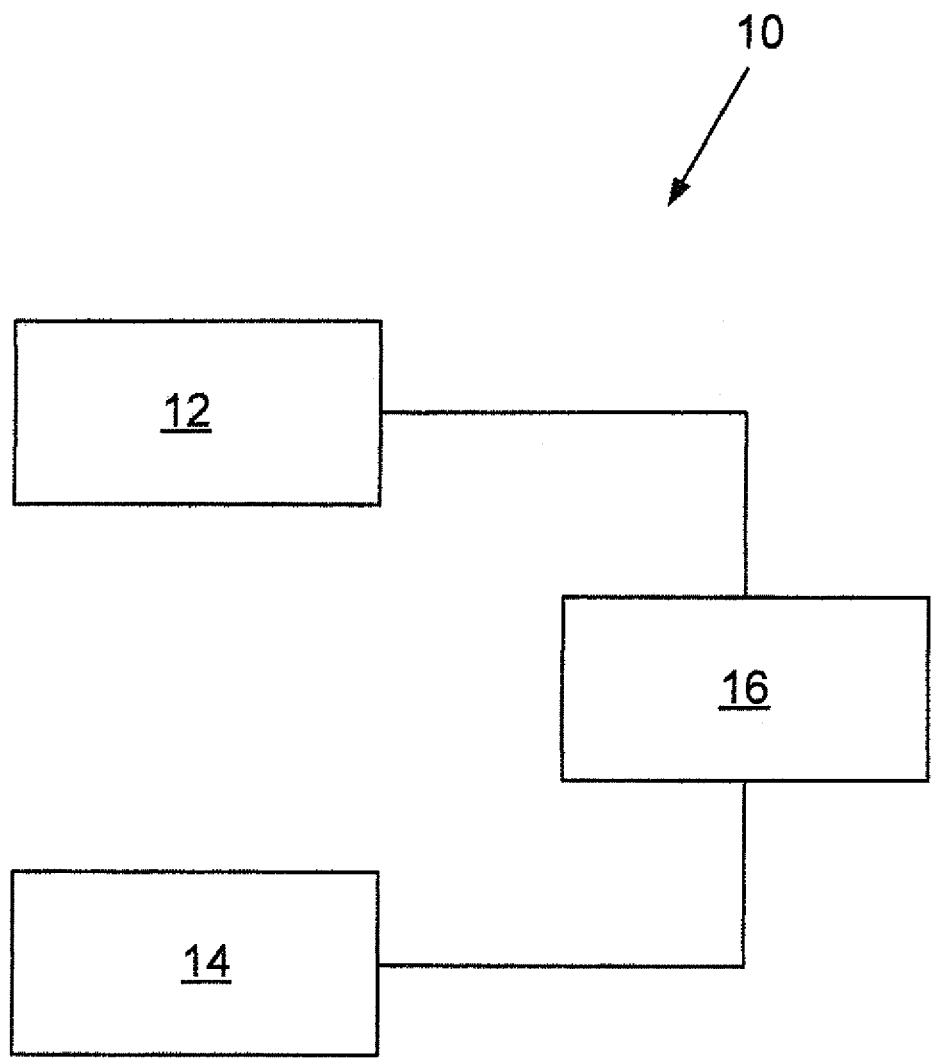
FIG. 1 is a schematic illustration showing a closed-loop therapy delivery system constructed in accordance with one aspect of the present disclosure.

The present disclosure relates to a system and method for precisely regulating endogenous neuromodulatory agent levels, and in particular to a closed-loop system and method for managing epilepsy and other neurological disorders. Adenosinergic neuromodulation plays a crucial role in control of seizure activity, and is described as the brain's endogenous anticonvulsant. Acute surges in adenosine (e.g., during treatment), however, can trigger several undesirable downstream effects. For example, surges in adenosine can lead to activation of immune-modulatory systems, thereby causing astrogliosis and epileptogenesis. Advantageously, the present disclosure provides a closed-loop system and method for precisely regulating (e.g., maintaining) the endogenous level of a neuromodulatory agent (e.g., a neurotransmitter, such as adenosine) within its normal physiological range, thereby mitigating or preventing undesirable side effects associated with abnormal endogenous levels of the neuromodulatory agent.

Unless otherwise defined, all technical terms used herein have the same meaning as commonly understood by one of ordinary skill in the art to which the present disclosure pertains.

In the context of the present disclosure, the term "endogenous" can refer to a substance or molecule that originates in, or is produced within, an organism, tissue or cell.

As used herein, the term "endogenous level" can refer to the level or concentration (e.g., $\mu M$, nM, etc.) of a neuromodulatory agent that originates in, or is produced within, a particular region (or regions) of a subject, such as an intraparenchymal region.

As used herein, the term "neuromodulatory agent" can refer to a broad class of chemical substances or molecules capable of signaling between nerve cells or neurons. In some instances, neuromodulatory agents may be capable of causing a change in neuronal activity, chemistry and/or metabolism. For example, the change(s) can refer to an increase, decrease, or even a change in a pattern of neuronal activity.

As used herein, the term "intraparenchymal target site" can refer to a region of subject's brain targeted for administration or delivery of one or more neuromodulatory agents thereto. In some instances, intraparenchymal administration can refer to administration directly to brain tissue. In other instances, intraparenchymal administration may be directed to any brain region where delivery of one or more neuromodulatory agents is effective to mitigate or prevent one or more of epilepsy, ictogenesis, epilpetogenesis, or other neurological disorder (e.g., Parkinson's disease, Alzheimer's disease). In one example, a neuromodulatory agent can be administered intraparenchymally to a region of a subject's brain proximate to, or within, an area of an epileptic focus.

As used herein, the term "epilepsy" can refer to any disorder in which a subject (e.g., a human adult, child or infant) experiences one or more seizures and/or tremors. Examples include, but are not limited to, epilepsy (including, but not limited to, localization-related epilepsies, generalized epilepsies, epilepsies with both generalized and local seizures, and the like), seizures as a complication of a disease or condition (such as seizures associated with encephalopathy, phenylketonuria, juvenile Gaucher's disease, Lundborg's progressive myoclonic epilepsy, stroke, head trauma, stress, hormonal changes, drug use or withdrawal, alcohol use or withdrawal, sleep deprivation, etc.), and the like. The term can also refer to the clinical disorder regardless of type of seizure, origin of seizure, progression of seizure or underlying cause or etiology.

As used herein, the term "subject" can refer to any warm-blooded organism including, but not limited to, human beings, pigs, rats, mice, dogs, goats, sheep, horses, monkeys, apes, rabbits, cattle, etc.

As used herein, the terms "treating" and "treat" can refer to therapeutically regulating, preventing, improving, alleviating the symptoms of, and/or reducing the effects or symptoms of a disease or condition, such as epilepsy, ictogenesis, epileptogenesis, neurological disorders (e.g., Parkinson's disease, Alzheimer's disease), and the like.

As used herein, the term "normal physiological range" can refer to the endogenous level or concentration of a neuromodulatory agent in a healthy or apparently healthy subject. Healthy or apparently healthy subjects can include those subjects who have not previously been diagnosed as having any signs or symptoms indicating the presence of epilepsy or a neurological disorder, a history of epilepsy or a neurological disorder, or evidence of epilepsy or a neurological disorder. Apparently healthy subjects may not otherwise exhibit symptoms of epilepsy or a neurological disorder. In other words, such subjects, if examined by a medical professional, would be characterized as healthy and free of symptoms of epilepsy or a neurological disorder.

Figure 2:
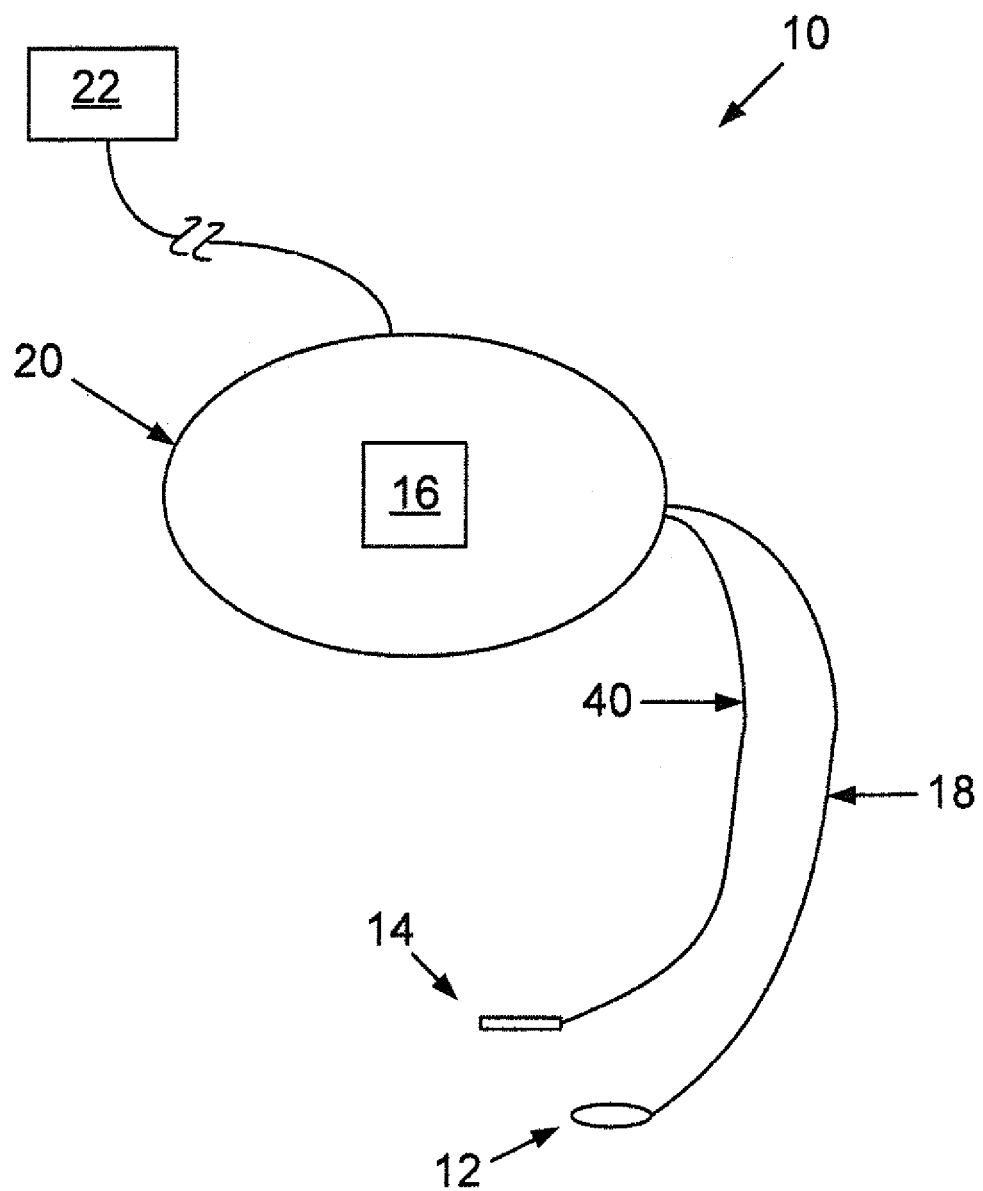
FIG. 2 is a schematic illustration showing one example of the closed-loop therapy delivery system in FIG. 1.

One aspect of the present disclosure is illustrated in FIG. 1 and includes a closed-loop therapy delivery system 10 for regulating an endogenous level of a first neuromodulatory agent in a subject. The therapy delivery system 10 includes a sensing component 12, a delivery component 14, and a controller 16 configured to coordinate operation of the sensing and delivery components. All or only a portion of the therapy delivery system 10 is implantable within the subject. One example of the therapy delivery system 10 is shown in FIG. 2. As described in more detail below, the therapy delivery system 10, and in particular the controller 16, is configured to automatically coordinate (e.g., without input from the subject or a third party) sensing and delivery of a second neuromodulatory agent to an intraparenchymal target site to precisely maintain the endogenous level of a first neuromodulatory agent within a normal physiological range.

In another aspect of the present disclosure, the sensing component 12 is configured to detect an extracellular level of a first neuromodulatory agent in a subject. In some instances, the sensing component 12 can include one or more sensors (not shown in detail) capable of detecting the level or concentration of a first neuromodulatory agent. In other instances, the sensor(s) comprising the sensing component 12 can include an electrochemical sensor capable of detecting a first neuromodulatory agent at a physiological or sub-physiological level. In further instances, the sensor(s) comprising the sensing component 12 can include an electrochemical sensor capable of detecting a first neuromodulatory agent (e.g., adenosine) at a physiological or sub-physiological level using fast-scan cyclic voltammetry and fixed potential amperometry. In one example, the sensing component 12 can include a carbon-fiber microelectrode. In another example, the sensing component 12 can include a carbon-fiber microelectrode configured to detect the level or concentration of adenosine at a sub-physiological level (e.g., about 15 nM). The sensor(s) comprising the sensing component 12 can be in electrical communication with the controller 16 and/or the delivery component 14 (e.g., via a lead 18 or leads). More detailed descriptions of sensors that may be employed as the sensing component 12, as well as other examples of sensors and feedback control techniques that may be employed are disclosed in U.S. Pat. No. 5,716, 377, which is hereby incorporated by reference in its entirety.

In another aspect of the present disclosure, the delivery component 14 is configured to deliver an amount of a second neuromodulatory agent to an intraparenchymal target site of the subject. The delivery component 14 can be in electrical communication with the sensing component 12 and/or the controller 16. In some instances, the delivery component 14 can include a drug port (not shown in detail) or other fluid conveying mechanism for delivering an amount of the second neuromodulatory agent to the intraparenchymal target site. The drug port or other fluid conveying mechanism can be fluidly connected to a pump 20, which is in further fluid communication with a reservoir 22 configured to store an amount of the second neuromodulatory agent. The reservoir 22 can be implanted within, or located remotely from, the subject. It will be appreciated that the therapy delivery system 10 can include one or more delivery components 14.

Any one or combination of neuromodulatory agents can be deliverable to the intraparenchymal target site. In some instances, the first and second neuromodulatory agents can be the same. In other instances, the first and second neuromodulatory agents can be different. In one example, the first and/or second neuromodulatory agent(s) can be a neurotransmitter. Examples of neurotransmitters can include, but are not limited to, serotonin, melatonin, epinephrine, norepinephrine, dopamine, adenosine and acetylcholine. In one example, the first and second neuromodulatory agents are adenosine. In another example, the first and second neuromodulatory agents are dopamine. In a further example, the first and second neuromodulatory agents are acetylcholine.

In another aspect of the present disclosure, the controller 16 (not shown in detail) is configured to coordinate operation of the sensing and delivery components 12 and 14. In some instances, the controller 16 can include circuitry (e.g., a microprocessor, memory, etc.) and software (e.g., one or more algorithms) in electrical communication with the sensing and delivery components 12 and 14. In some instances, the controller 16 (e.g., the software) is pre-programmed to selectively control the infusion or delivery rate of the second neuromodulatory agent based on the detected endogenous level of the first neuromodulatory agent. The controller 16 can be disposed on, or integrally formed with, a pump 20. In some instances, the controller 16 and the pump 20 are assembled as part of a hermetically-sealed housing (not shown). The controller 16 can be powered by a power source (not shown), such as a battery. The power source may be positioned in any suitable location, such as integrated as part of the therapy delivery system 10, adjacent or integrated with the controller 16, at a remote site in or on the subjects body, and/or away from the subject's body in a remote location.

It will be appreciated that the therapy delivery system 10 can operate in conjunction with external equipment (not shown). The therapy delivery system 10 is mostly autonomous (particularly when performing its usual sensing, detection, and delivery functions), but can additionally or optionally include a selectable wireless link (not shown) to external equipment, such as a programmer (not shown). In some instances, the programmer can be used to manually control operation of the therapy delivery device 10, as well as to transmit information to, or receive information from, the controller 16. In other instances, the programmer may specify and set variable parameters in the therapy delivery system 10 (e.g., flow rate) to adapt the function of the therapy delivery system to meet the subject's needs.

Figure 3:
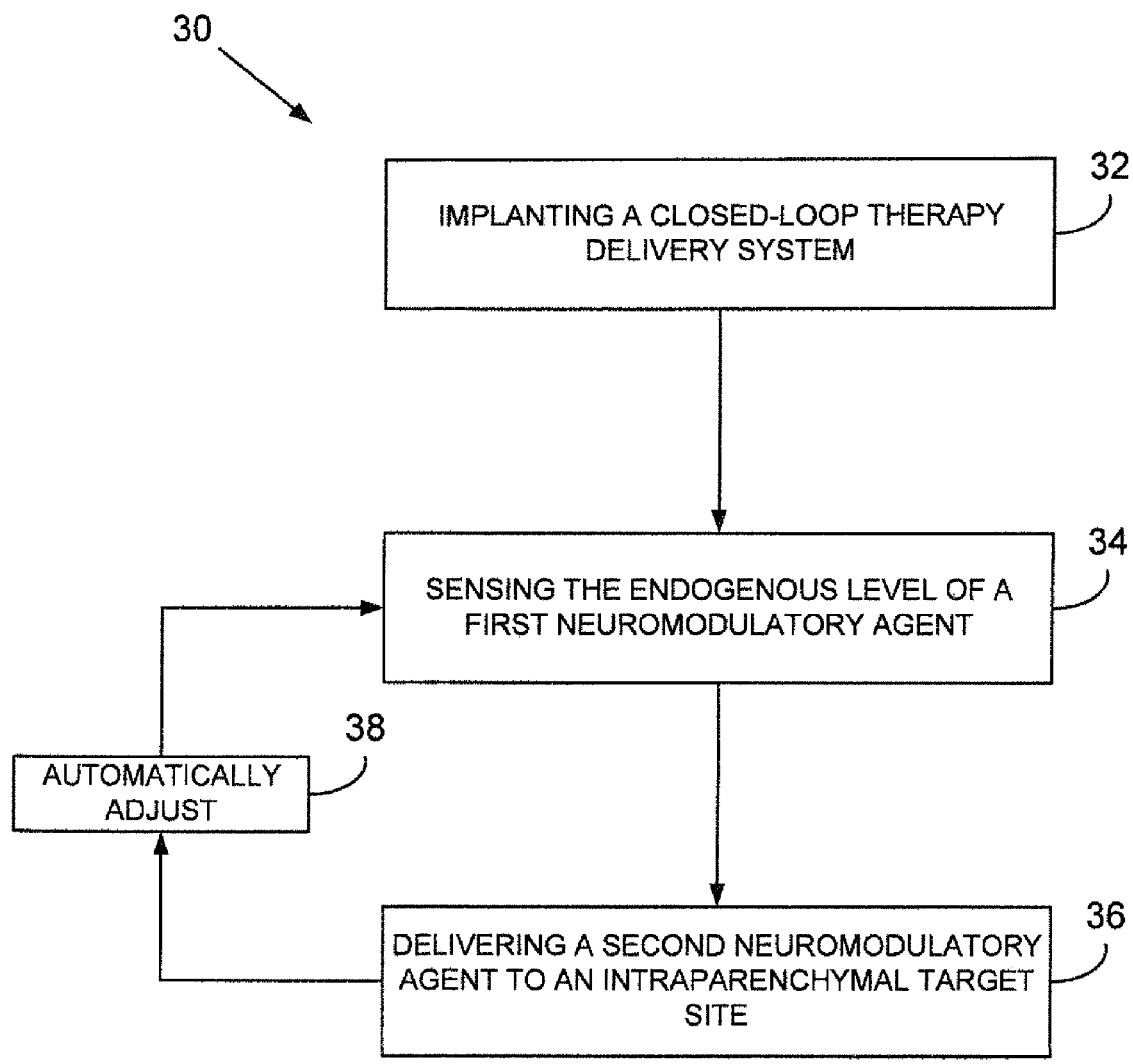
FIG. 3 is a process flow diagram illustrating a method for regulating the level of an endogenous first neuromodulatory agent in a subject according to another aspect of the present disclosure.

Another aspect of the present disclosure is illustrated in FIG. 3 and includes a method 30 for regulating an endogenous level of a first neuromodulatory agent in a subject. The method 30 generally includes the following steps: implanting a closed-loop therapy delivery system 10 in a subject (Step 32); sensing, by a sensing component 12 of the therapy delivery system, the endogenous level of the first neuromodulatory agent (Step 34); activating a delivery component 14 of the therapy delivery system to adjust application of a second neuromodulatory agent in response to the sensed level of the first neuromodulatory agent (Step 36); and automatically repeating Steps 34 and 36 until the endogenous level of the first neuromodulatory agent is within a normal physiological range (Step 38).

In some instances, the method 30 can be employed to prevent or mitigate epilepsy, or a symptom associated therewith, in the subject. In one example, the method 30 can be employed to mitigate or prevent at least one of ictogenesis and epileptogenesis in the subject. Ictogenesis and epileptogenesis have unique differences. On one hand, ictogeneiss (the initiation and propagation of a seizure in time and space) is a rapid electrical/chemical event occurring over seconds or minutes. On the other hand, epileptogenesis (the gradual process whereby normal brain is transformed into a state susceptible to spontaneous, episodic, time-limited recurrent seizures through the initiation and maturation of an epileptogenic focus) is a slow biochemical/histological process occurring over months to years. In other instances, the method 30 can be employed to prevent or mitigate a neurological disorder in the subject. The neurological disorder can be characterized by an overabundance or underabundance of a neurotransmitter, such as dopamine or acetylcholine (as compared to a healthy or apparently healthy subject). In one example, a neurological disorder treatable by the method 30 can include Alzheimer's disease. In another example, a neurological disorder treatable by the method 30 can include Parkinson's disease.

Figure 4:
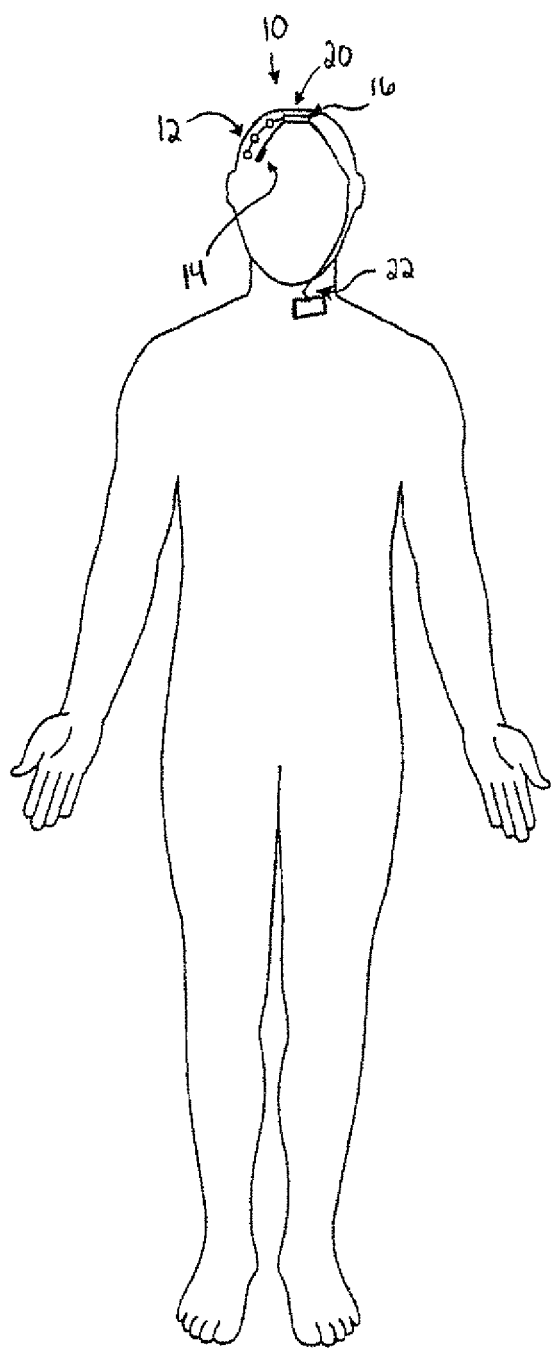
FIG. 4 is a schematic illustration showing a closed-loop therapy delivery system of the present disclosure implanted in a subject.

At Step 32, the therapy delivery system 10 is implanted in the subject. In one example, all or only a portion of the therapy delivery system 10 can be implanted intracranially (FIG. 4). In some instances, the therapy delivery system 10 can be surgically implanted so that the sensing component 12 and the delivery component 14 are each positioned in or about an intraparenchymal target site. Examples of intraparenchymal target sites can include, but are not limited to, the hippocampus, amygdala, anterior nucleus of the thalamus, centromedian nucleus of the thalamus, other portion of the thalamus, subthalamic nucleus, motor cortex, premotor cortex, supplementary motor cortex, other motor cortical areas, somatosensory cortex, other sensory cortical areas, Wernicke's area, Broca's area, pallido-thalamic axons, lenticulo-thalamic fiber pathway, substantia nigra pars reticulata, basal ganglia, external segment of globus pallidus, subthalalmic to pallidal fiber tracts, putamen, putamen to PGe fibers, other areas of seizure focus, other cortical regions, or combinations thereof.

In other instances, the controller 16 and/or pump 20 (which may be contained in a hermetically-sealed housing) can be situated on the outer surface of the cranium (and under the subject's scalp). The sensing and delivery components 12 and 14 can then extend (e.g., via leads 18 or fluid conduits 40) from the controller 16 and/or pump 20, across the cranium, and through one or more burr holes or other cranial openings into the subject's brain. In the brain, the sensory component 12 and the delivery component 14 can be positioned in or about the intraparenchymal target site. It will be appreciated that positioning the controller 16 and/or pump 20 near the intraparenchymal target site allows shorter leads 18 or fluid conduits 40 to be used between the sensing and delivery components 12 and 14 and the controller and/or pump, thereby reducing the risk of mechanical failure as well as surgical complexity and scope. It will also be appreciated that placement of the sensing and delivery components 12 and 14 is subject specific; that is, different symptoms and conditions call for different structures to be targeted.

In one example, a subject suffering from epilepsy may benefit from intrahippocampal placement of the sensing and delivery components 12 and 14. For instance, first and second pairs of sensing and delivery components 12 and 14 may be separately implanted in both hippocampi. The first pair of sensing and delivery components 12 and 14 can comprise an electrochemical sensor (e.g., a carbon-fiber microelectrode) and a drug port configured to detect and deliver adenosine, respectively, in the left hippocampus. Similarly, the second pair of sensing and delivery components 12 and 14 can comprise an electrochemical sensor (e.g., a carbon-fiber microelectrode) and a drug port configured to detect and deliver adenosine, respectively, in the right hippocampus.

After implantation of the therapy delivery system 10, the sensing component 12 can detect the endogenous level or concentration of the first neuromodulatory agent at the intraparenchymal target site (Step 34). In one example, the sensing component 12 can detect the level or concentration of endogenous adenosine at the intraparenchymal target site (e.g., an intrahippocampal target site). Based on the detected level or concentration of the first neuromodulatory agent, the sensing component 12 can generate a sensor signal, which is then relayed to the controller 16.

Once the sensor signal is received, the signal can be processed by the controller 16, which in turn generates an activation signal. The activation signal encodes functional information related to delivery of the second neuromodulatory agent, such as volume and rate parameters. The activation signal is relayed to the delivery component 14, resulting in delivery of the second neuromodulatory agent at the intraparenchymal target site (e.g., at a prescribed volume and rate). In one example, the delivery component 14 can deliver a desired amount of adenosine at the intraparenchymal target site at a desired rate.

Steps 34 and 36 can be automatically repeated until the endogenous level of the first neuromodulatory agent is within a normal physiological range (Step 38). The rate and volume of the second neuromodulatory agent that is automatically delivered to the intraparenchymal target site will depend upon the detected level or concentration of the first neuromodulatory agent. For instance, where the detected level or concentration of the first neuromodulatory agent is below the normal physiological range, the second neuromodulatory agent can be continuously delivered to the intraparenchymal target site until the level or concentration of the first neuromodulatory agent is within the normal physiological range. Thus, the rate and volume of the second neuromodulatory agent delivered to the intraparenchymal target site can vary depending upon fluctuations in the endogenous level or concentration of the first neuromodulatory agent.

In one example, the delivery component 12 can deliver adenosine to an intraparenchymal target site, such as an intrahippocampal target site. The endogenous concentration or level of adenosine at the intrahippocampal target site can be detected by the sensing component 12. If the detected level or concentration of adenosine is below the normal physiological range (20 nM to 300 nM), the controller 16 can activate the pump 20 and cause a desired amount of adenosine to be delivered to the intrahippocampal target site (at a desired rate) until the detected level or concentration of endogenous adenosine is within the normal physiological range.

Advantageously, the method 30 permits precise control over the level of adenosine at the intraparenchymal target site, thereby avoiding an acute surge in adenosine concentration. Consequently, triggering of immune-modulatory systems that cause astrogliosis and epileptogenesis may be prevented or mitigated. Additionally, precise control over endogenous adenosine levels may also result in anti-ictogenic and antiepileptic effects by normalizing local neurotransmitter levels, thereby stopping the mechanisms that recruit other parts of the brain from becoming involved in epilepsy.

From the above description of the invention, those skilled in the art will perceive improvements, changes and modifications. Such improvements, changes, and modifications are within the skill of the art and are intended to be covered by the appended claims.

Having described the invention, the following is claimed:

1. A method for regulating level of endogenous adenosine in a subject, said method comprising the steps of:
   (a) implanting a closed-loop therapy delivery system in the subject, the therapy delivery system including at least one sensing component, a delivery component, and a controller configured to coordinate operation of the sensing component and the delivery component;
   (b) sensing, by the sensing component, the level of endogenous adenosine;
   (c) activating the delivery component to adjust delivery of adenosine to the intraparenchymal target site of the subject in response to the sensed level of the endogenous adenosine; and
   (d) automatically repeating steps (b) and (c) until the level of the endogenous adenosine is within a normal physiological range.

2. The method of claim 1, wherein the sensing component is configured to use fast-scan cyclic voltammetry (FSCV) and fixed potential amperometry (FPA) to detect the level of the endogenous adenosine.

3. The method of claim 1, wherein delivery of the adenosine prevents or mitigates ictogenesis.

4. The method of claim 1, wherein delivery of the adenosine prevents or mitigates epileptogenesis.

5. The method of claim 1, wherein delivery of adenosine to the intraparenchymal target site comprises delivery of adenosine to an intrahippocampal target site of the subject.

* * * * *